(12) United States Patent
Kim

(10) Patent No.: US 6,432,036 B1
(45) Date of Patent: Aug. 13, 2002

(54) DEVICE FOR MAGNETIC FOCUS RADIATION MEDICAL TREATMENT

(76) Inventor: Chi-Kyung Kim, 8-301 Samsung Villa, 173 Sangil-dong, Kangdong-gu, Seoul (KR)

(*) Notice: Subject to any disclaimer, the term of this patent is extended or adjusted under 35 U.S.C. 154(b) by 56 days.

(21) Appl. No.: 09/657,459

(22) Filed: Sep. 7, 2000

(30) Foreign Application Priority Data

Dec. 15, 1999 (KR) ............................................. 99-58024

(51) Int. Cl.[7] .......................... A61N 2/00; A61H 23/00
(52) U.S. Cl. ......................................... 600/9; 601/108
(58) Field of Search ..................... 600/1–12; 601/108, 601/134; 606/189; 128/107

(56) References Cited

U.S. PATENT DOCUMENTS

| | | | | |
|---|---|---|---|---|
| 4,161,943 A | * | 7/1979 | Nogier | 600/12 |
| 4,508,119 A | * | 4/1985 | Tukamoto | 606/189 |
| 5,140,979 A | * | 8/1992 | Nakagawa | 601/108 |
| 5,162,037 A | * | 11/1992 | Whitson-Fischman | 600/12 |
| 5,676,684 A | | 10/1997 | Choi | |
| 5,741,291 A | * | 4/1998 | Yoo | 606/189 |
| 5,788,657 A | * | 8/1998 | Burns | 601/134 |
| 5,792,176 A | | 8/1998 | Chang | |
| 5,904,700 A | * | 5/1999 | Guo | 606/189 |
| 5,950,239 A | | 9/1999 | Lopez | |
| 5,965,282 A | | 10/1999 | Baermann | |
| 6,050,931 A | | 4/2000 | Russell | |
| 6,113,620 A | * | 9/2000 | Chung | 606/189 |

FOREIGN PATENT DOCUMENTS

| | | | | |
|---|---|---|---|---|
| CA | 1236603 A | * | 12/1999 | A61H/7/00 |
| KR | 0133133 | | 12/1997 | |
| KR | 10-0198982 | | 3/1999 | |

OTHER PUBLICATIONS

Alta Vista Search, Function . The Genesen Acutouch point stimulator was invented by Dr. Chi Kyung Kim of the Korean Industrial Engineering Center. The Genesen was . . . www.acutouch.com/function.htm.

Alta Vista Search, 2.htm–Introduction to Genesen, Introduction. Establishment of Genesen Medical Center. (YeonBin University Medical Hospital in China) the Genesen Medical Center was established in . . . www.genesen.com/2.htm.

* cited by examiner

Primary Examiner—Eric F. Winakur
Assistant Examiner—Nikita Veniaminov
(74) Attorney, Agent, or Firm—Robert E. Bushnell, Esq.

(57) ABSTRACT

A device for magnetic focus radiating medical treatment is disclosed. The device has a support member holding both a magnet and a needle therein in a way such that the magnet comes into contact with the needle. The magnet is used for generating lines of magnetic force, while the needle is used for radiating the lines of magnetic force from the magnet onto a desired part of the human body. A hollow casing receives the support member therein with the tip of the needle being selectively projected from the lower end of the casing. This casing has an external thread at its lower end. An outside plug detachably covers the top end of the casing. A cap is movably tightened to the external thread of the casing. This cap also has a needle hole at a central portion of its wall so as to allow the needle to pass through the needle hole. In the above device, the exposed length of the needle outside the cap is adjustable as desired by appropriately tightening or loosening the internally threaded cap relative to the externally threaded casing.

22 Claims, 8 Drawing Sheets

DEVICE FOR MAGNETIC FOCUS RADIATION MEDICAL TREATMENT

CLAIM OF PRIORITY

This application makes reference to, incorporates the same herein, and claims all benefits accruing under 35 U.S.C. §119 from my application A DEVICE FOR ACUPUNCTURE filed with the Korean Industrial Property Office on Dec. 15, 1999 and there duly assigned Ser. No. 58024/1999.

BACKGROUND OF THE INVENTION

1. Field of the Invention

The present invention relates, in general, to a device for magnetic focus radiation medical treatment, designed to radiate a large quantity of healthful far infrared rays, anions and lines of magnetic force, and, more particularly, to a structural improvement in such a medical treatment device to directly apply the healthful far infrared rays, anions and lines of magnetic force onto the human body and to allow a user to freely adjust the length of an acupuncture needle as desired.

2. Description of the Related Art

Many workers skilled in the art believe that devices for magnetic focus radiation medical treatment may cure disease by stimulating the spots on the human body suitable for acupuncture. Since there is a widespread belief that radiation of far infrared rays, anions and lines of magnetic force onto a specified area on the human body is very healthful to the human body, several types of devices for magnetic focus radiation medical treatment have been proposed and used. Examples of such devices are seen in the following U.S. Patents.

U.S. Pat. No. 5,676,684, to Choi, entitled METHOD AND APPARATUS FOR ACUPUNCTURE-TAPPING PORTION OF HUMAN, describes an acupuncture tapping plate which has attached needles, where the needles may be magnetic.

U.S. Pat. No. 5,792,176, to Chang, entitled ACUPRESSURE PATCH AND METHOD OF USE, describes an acupressure patch for providing controlled pressure to a selected point on the skin. The acupressure patch may contain a magnet.

U.S. Pat. No. 5,904,700, to Guo, entitled MAGNETIC ACUPUNCTURE POINTER, describes an acupuncture pointer which includes a permanent magnetic head.

U.S. Pat. No. 5,950,239, to Lopez, entitled MAGNETIC TREATMENT CLOTHING, describes therapeutic clothing having magnets at positions designed to correspond to shiatsu body points.

U.S. Pat. No. 5,965,282, to Baermann, entitled MAGNETIC ARRANGEMENT FOR THERAPEUTIC APPLICATION, describes an arrangement of magnets near the skin, and discusses the use of magnets at acupuncture points.

U.S. Pat. No. 6,050,931, to Russell, entitled MAGNETIC THERAPEUTIC DEVICE FOR ARTHRITIC FINGERS, describes a device with small lightweight permanent magnets encased in a stretchable resin carrier held on the finger and joints of the hand.

However, conventional medical treatment devices are problematic in that they separately radiate far infrared rays, anions and lines of magnetic force.

In an effort to overcome the problem experienced in such conventional treatment devices, the inventor of this invention proposed a device for magnetic focus radiation medical treatment in Korean Patent Nos. 133,133 and 198,982. This device is designed to radiate the desired far infrared rays, anions and lines of magnetic force from one device at the same time and to radiate the highly intense far infrared rays, anions and lines of magnetic force onto a desired part of the human body while achieving structural compactness of the device.

SUMMARY OF THE INVENTION

It is therefore an object of the present invention to provide an improved acupuncture device.

A further object of the present invention is to provide an improved magnetic treatment device.

A still further object of the present invention is to provide an acupuncture device providing less painful or less stimulating therapy.

A yet further object of the invention is to provide a magnetic acupuncture device which is compact.

Accordingly, the present invention has been made keeping in mind the above problems occurring in the prior art, and an object of the present invention is to provide a device for magnetic focus radiation medical treatment, which has a cap designed to allow a user to freely adjust the exposed length of an acupuncture needle of the device as desired.

Another object of the present invention is to provide a device for magnetic focus radiation medical treatment, which has a cap provided with a radiation means for radiating desired far infrared rays, anions and lines of magnetic force, thus effectively radiating and focusing a large quantity of far infrared rays, anions and lines of magnetic force onto a desired part of the human body.

A further object of the present invention is to provide a device for magnetic focus radiation medical treatment, which has a cap safely covering the acupuncture needle when a user carries the device, thus protecting the needle from external impact.

Still another object of the present invention is to provide a device for magnetic focus radiation medical treatment, which has a compact structure and is provided with a radiation means for radiating a large quantity of far infrared rays, anions and lines of magnetic force onto a desired part of the human body without allowing a leakage of such infrared rays, anions or lines of magnetic force.

Still another object of the present invention is to provide a device for magnetic focus radiation medical treatment, which is designed to allow a plurality of devices for magnetic focus radiation medical treatment to be usable at the same time while being easily and simply coupled together.

In order to accomplish the above objects, the present invention provides a device for magnetic focus radiating medical treatment, comprising: a support member holding both a magnet and a needle therein in a way such that the magnet comes into contact with the needle. This magnet is used for generating lines of magnetic force, while the needle is used for radiating the lines of magnetic force from the magnet onto a desired part of the human body. A hollow casing, having a predetermined length, receives the support member therein, with the tip of the needle being selectively projected from the lower end of the casing. This casing has an external thread at its lower end. An outside plug detachably covers the top end of the casing. A cap is movably tightened to the external thread of the casing. This cap has an internal thread at its upper portion and movably engages with the external thread of the casing at the internal thread.

The cap also has a needle hole at a central portion of its wall so as to allow the needle to pass through the needle hole. In the above device, the exposed length of the needle outside the cap is adjustable as desired by appropriately tightening or loosening the internally threaded cap relative to the externally threaded casing.

In an embodiment, the support member is an integrated body composed of upper, middle and lower parts, with a magnet holding part provided at the upper part and a needle holding part provided at the lower part while communicating with the magnet holding part. The upper and lower parts of the support member are tapered, with an annular step part being formed on the middle part at a position around a junction between the middle and lower parts, the support part also having a plurality of axial grooves extending on the external surface of the support part at positions covering the middle part and the annular step part. The axial grooves of the middle part communicate with the axial grooves of the annular step part while being leveled with each other at their bottom surfaces.

The support member is fitted into a coupling member at its upper and middle parts prior to being set within the casing, with both the annular step part of the support member being seated on the end of the coupling member and an inside cap detachably covering the top end of the coupling member. In the present invention, the coupling member is preferably made of aluminum.

The above support member and the cap are made of at least one material selected from the group consisting of an anion emitting material, a far infrared ray emitting material and a mixture thereof. A reflection tap, made of aluminum, is detachably fitted into the top end of the support member, with a gap being formed between the lower part of the support member and an internal surface of the casing, and so anions or far infrared rays emitted from the support member are reflected by the reflection tap and are radiated through both the axial grooves of the middle and annular step parts of the support member and the gap formed between the lower part of the support member and the internal surface of the casing.

In the device of this invention, a first annular magnet may be set within the hollow casing at a position around the lower end of the casing. A second annular magnet is set within the cap at a position around the needle hole of the cap.

In an embodiment, at least one axial fitting channel is formed on the external surface of the casing by two parallel guide rails. One of the two parallel guide rails are projected inwardly along its top edge and a stop being formed at the lower end of the fitting channel.

The axial fitting channel of the casing axially selectively receives a first side edge of a connection plate therein, with a second side edge of the connection plate being fitted into the axial fitting channel of another casing, thus coupling two or more devices into a single system.

The support member is sectioned into a magnet support part and a needle support part, the magnet and needle support parts part being continued and integrated into a single body at a junction between them.

BRIEF DESCRIPTION OF THE DRAWINGS

A more complete appreciation of the invention, and many of the attendant advantages, thereof, will be readily apparent as the same become letter understood by reference to the following detailed description when considered in conjunction with the accompanying drawings in which like reference symbols indicate the same or similar components, wherein.

DETAILED DESCRIPTION OF THE PREFERRED EMBODIMENTS

Figure 1:
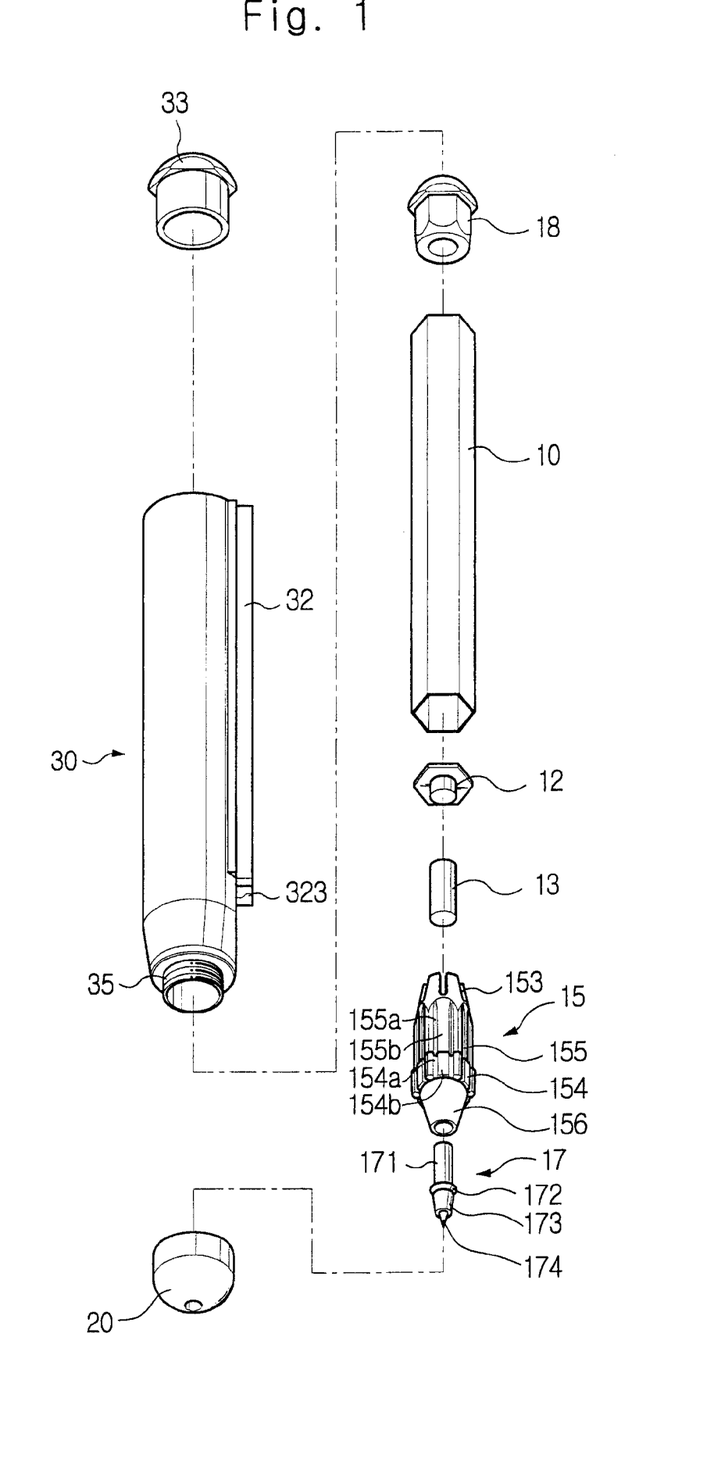
FIG. 1 is an exploded perspective view of a device for magnetic focus radiation medical treatment in accordance with the preferred embodiment of the present invention.
Figure 2:
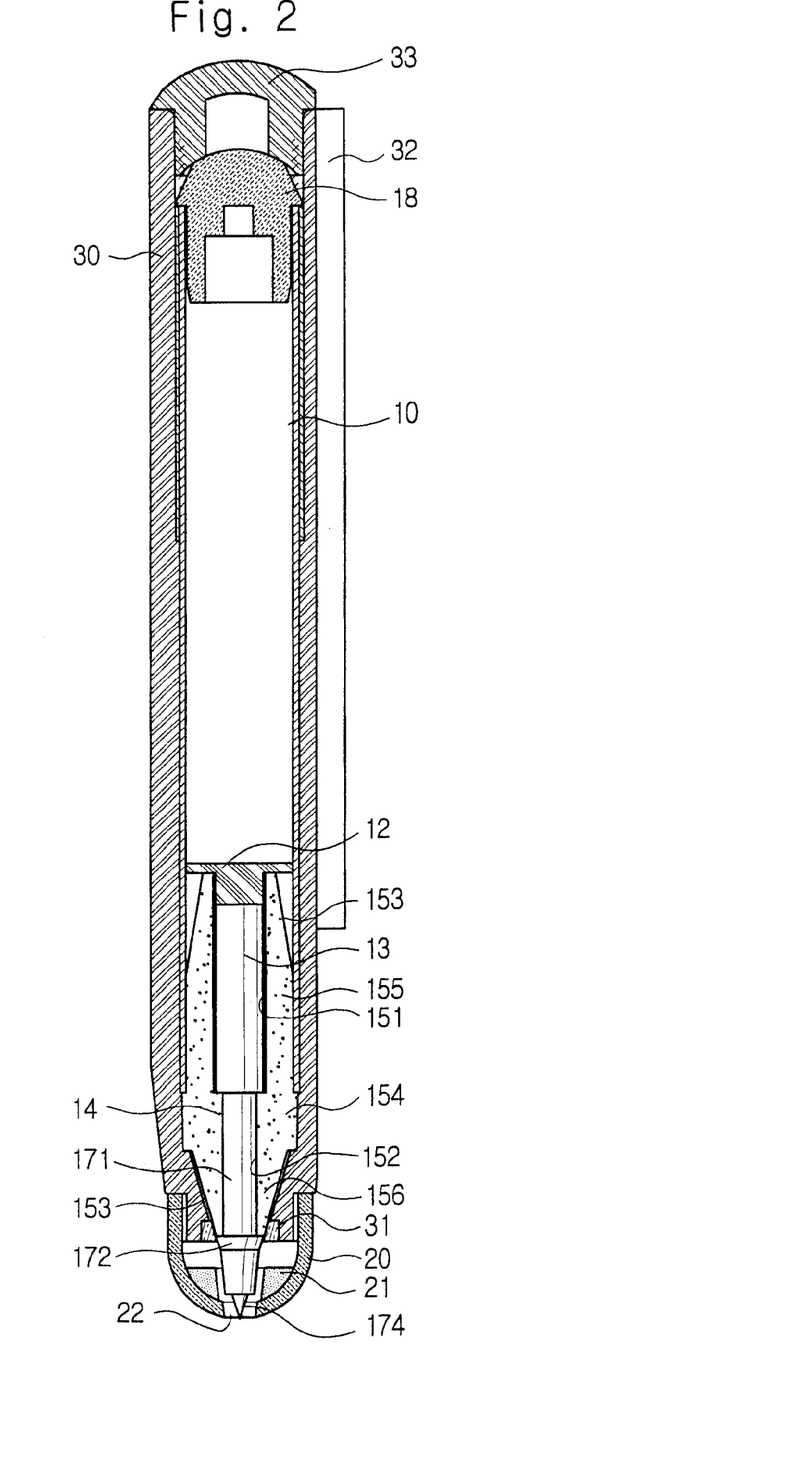
FIG. 2 is a sectional view of the device for magnetic focus radiation medical treatment of FIG. 1, with all of the parts of the device being completely assembled together into a single body.

FIG. 1 is an exploded perspective view of a device for magnetic focus radiation medical treatment according to the preferred embodiment of this invention, while FIG. 2 is a sectional view of the device of FIG. 1, with the parts of the device being completely assembled together into a single body.

As shown in the drawings, the treatment device of this invention includes a support member 15, which is fly inserted into a coupling member 10 upwardly from the lower end of the coupling member 10. The above coupling member 10 is preferably made of aluminum and preferably has a hollow pipe shape having a hexagonal cross-section. An internal cap 18 is fitted into the top end of the above coupling member 10.

The above support member 15 is made of material capable of emitting far infrared rays and anions, with a magnet seat hole 151 being axially formed at the top end of the support member 15 to have a predetermined depth. A magnet 13, for example, a permanent magnet, is seated in the magnet seat hole 151 of the support member 15. A needle seat hole 152 is axially formed at the lower end of the support member 15, thus holding an acupuncture needle 17 therein. For ease of manufacture of the device, it is possible to design both the magnet seat hole 151 and the needle seat hole 152 to allow the two holes 151 and 152 to linearly communicate with each other. In such a case, it is preferable to design the diameter of the needle seat hole 152 to be smaller than that of the magnet seat hole 151, and so a step is formed at the junction between the two holes 151 and 152 with the magnet 13 being stably seated on the step within the magnet seat hole 151.

The above support member 15 has a hexagonal profile corresponding to the hexagonal cross-section of the coupling member 10. This support member 15 is an integrated body, with an upper taper part 153, a middle part 155, an annular step part 154 and a lower taper part 156 being orderly integrated into a single body. The upper taper part 153 is axially and regularly slitted, thus forming a plurality of axial pieces allowing an easy installation of both a reflection tap 12 and the magnet 13 into the support member 15.

Figure 3:
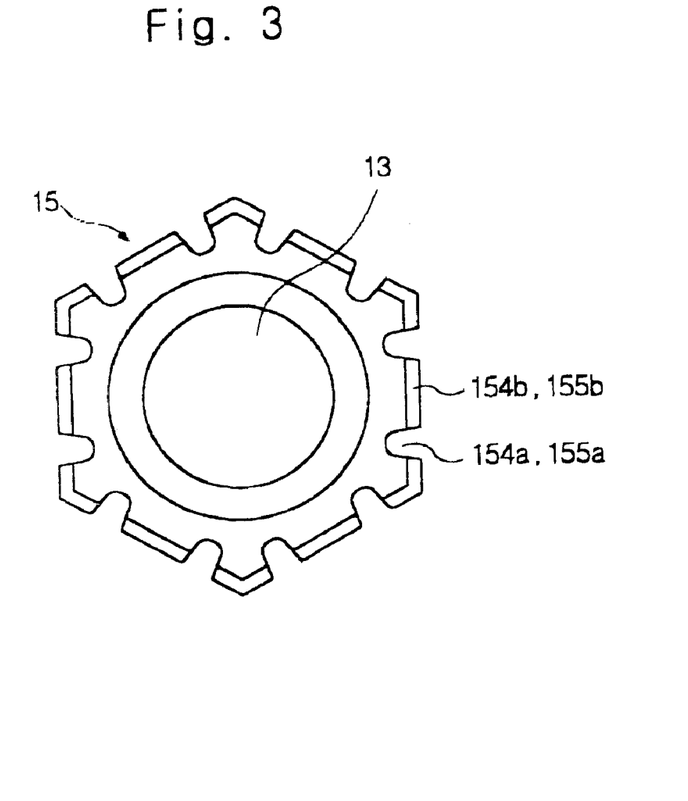
FIG. 3 is a sectional view of a support member of the treatment device of FIG. 1.

As shown in FIG. 3, a plurality of axial grooves 154a and 155a are regularly formed on the external surface of the support member 15 at positions around both the annular step part 154 and the middle part 155. In the above support member 15, each axial groove 155a of the middle part 155 communicates with an associated axial groove 154a of the annular step part 154, with the bottom surface of each axial groove 155a leveled with the bottom surface of an associated axial groove 154a of the annular step part 154. However, the level of the external surface 155b of the middle part 155 is lower than the level of the external surface 154b of the annular step part 154. That is, a step is formed at the junction between the external surfaces of the two parts 154 and 155. The height of the above step is equal to the thickness of the coupling member 10. In addition, the outer diameter of the middle part 155 is nearly equal to the inner diameter of the coupling member 10. When the middle part 155 of the support member 15 is inserted into the coupling member 10 upwardly from the lower end of the coupling member 10, the depth of insertion of the support member 15 into the coupling member 10 is limited since the step, formed at the junction between the middle part 155 and the annular step part 154, is stopped by the end of the coupling member 10 during the insertion of the support member 15 into the coupling member 10. In such a case, a plurality of axial channels 157 are regularly formed on the external surface of the support member 15 by the continued grooves 155a and 154a. Such an insertion of the support member 15 into the coupling member 10 will be described in more detail later herein.

The reflection tap 12 is downwardly inserted into the top end of the upper taper part 153 of the support member 15, thus being firmly installed within the part 153. The above reflection tap 12 is made of aluminum and reflects the anions or far infrared rays radiated from the support member 15. The reflected anions or far infrared rays from there reflection tap 12 pass through the channels 157 of the support member 15 prior to being introduced into the gap between the external surface of the lower taper part 156 and the internal surface of the casing 30. The construction of the casing 30 will be described in detail later herein.

An acupuncture needle 17 is inserted into the needle seat hole 152 from the lower end of the support member 15. This needle 17 includes a shank 171 and a sharpened tip 174. The shank 172 of the needle 17 is seated in the needle seat hole 152 of the support member 15, while the sharpened tip 174 is axially integrated with the lower end of the shank 172. An annular flange 172 is formed on the shank 171 at a predetermined position, thus limiting the depth of the shank 171 inserted into the needle seat hole 152 of the support member 15. In addition, it is preferable to taper the shank 171 in a direction from the lower end to the upper end of the shank 171. The tip 174 has to be precisely sharpened since it comes into direct contact with the skin of the human body.

An assembly, formed by installing the parts, such as the support member 15, into the coupling member 10, is inserted into the cylindrical casing 30 downwardly from the top end of the casing 30. The interior of the above casing 30 has a profile corresponding to the external profile of the coupling member 10. An external thread 35 is formed on the external surface of the lower end portion of the casing 30. In the preferred embodiment of this invention of FIG. 1, the lower end portion of the casing 30 is formed to have a diameter smaller than that of the remaining part of the casing 30 prior to forming the external thread 35 on the lower end portion of the casing 30. An outside plug 33 is fitted into the top end of the cylindrical casing 30. Axially formed along the external surface of the casing 30 is a fitting channel 32 having a predetermined length, with a stop 323 being formed at the lower end of the channel 32.

Figure 4:
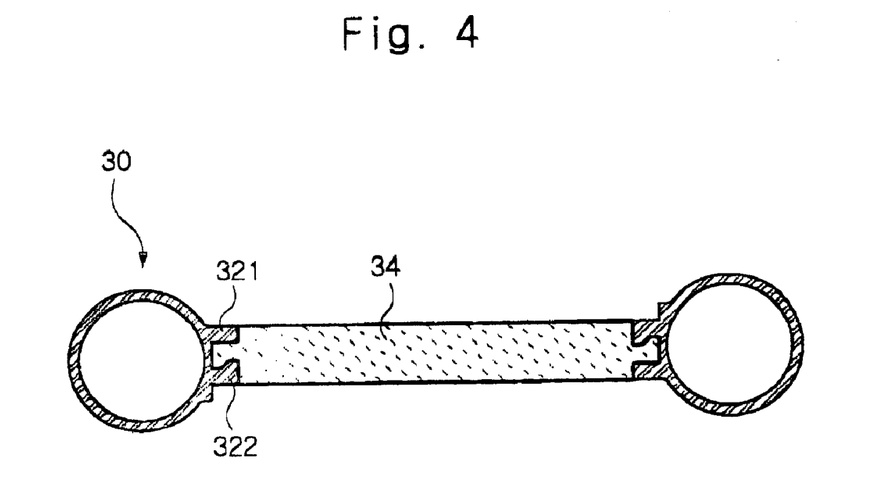
FIG. 4 is a sectional view, showing the construction of a coupling groove formed on a casing of the treatment device of this invention and used for coupling two devices of this invention to each other into a single system using a connection plate.

As shown in FIG. 4, the axial fitting channel 32 is defined by two parallel guide rails 321 and 322. When it is necessary to couple two devices of this invention to each other into a single system so as to use the two devices at the same time, opposite edges of a connection plate 34 are fitted into the axial fitting channels 32 of the two devices. One of the two parallel guide rails 321 and 322 is projected inwardly along its top edge, thus forming a linear hook capable of firmly catching an associated edge of the connection plate 34 without allowing the edge to be undesirably removed from the fitting channel 32. On the other hand, the stop 323 of the fitting channel 32 stops the lower corner of the connection plate 34, thus preventing the plate 34 from being undesirably and downwardly removed from the channel 32.

The two devices of this invention are coupled to each other into a single system as follows. That is, the two devices are primarily arrayed in parallel, with the fitting channels 32 of them being directly opposed to each other. Thereafter, opposite edges of connection plate 34 carefully inserted into the fitting channels 32 of the two devices downwardly from the 34 are thus stably and fully fitted into the channels 32 under the guide of the guide rails 321 and 322 until they are stopped by the stops 323 formed at the lower ends of the channels 32. The two devices are thus coupled together into a single system.

Figure 6:
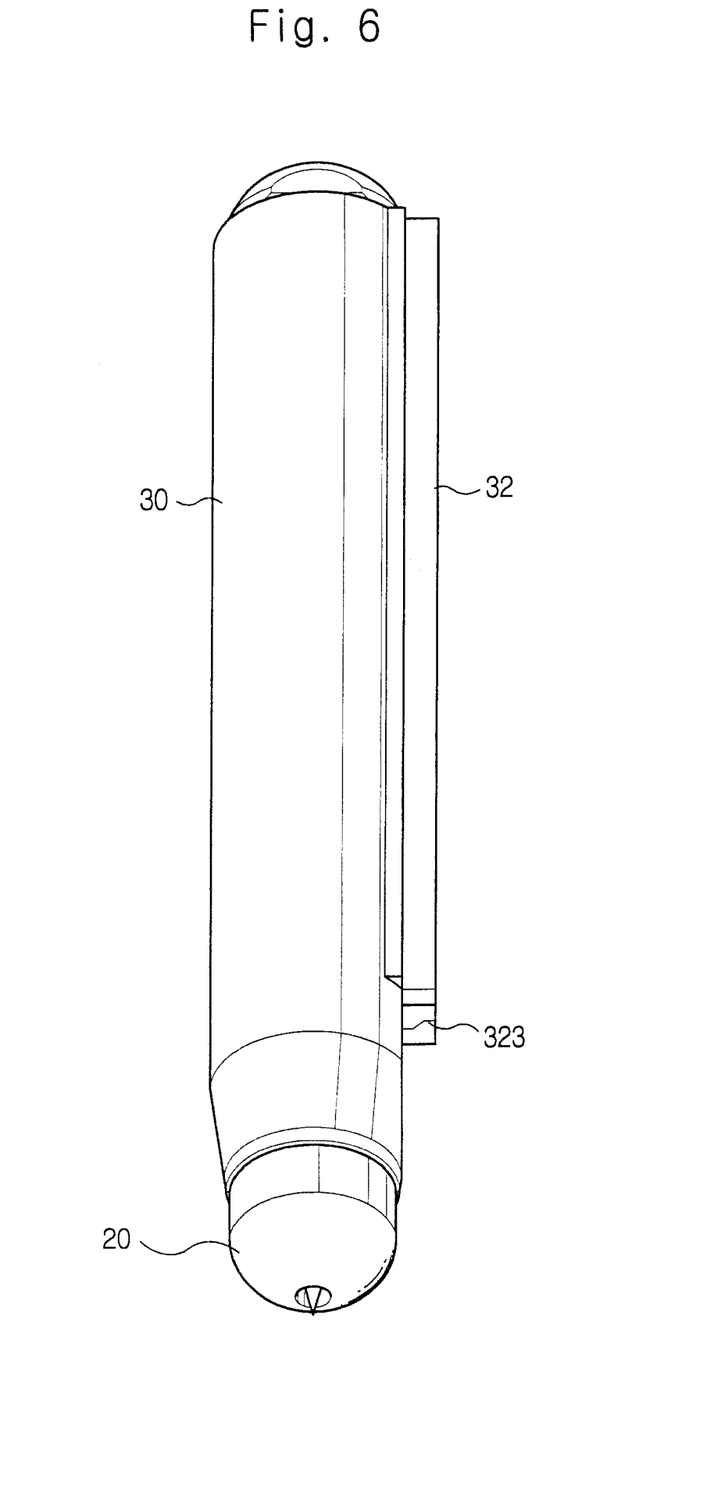
FIG. 6 is a perspective view, showing a cap tightened to the lower end of the casing of the treatment device of this invention.
Figure 8:
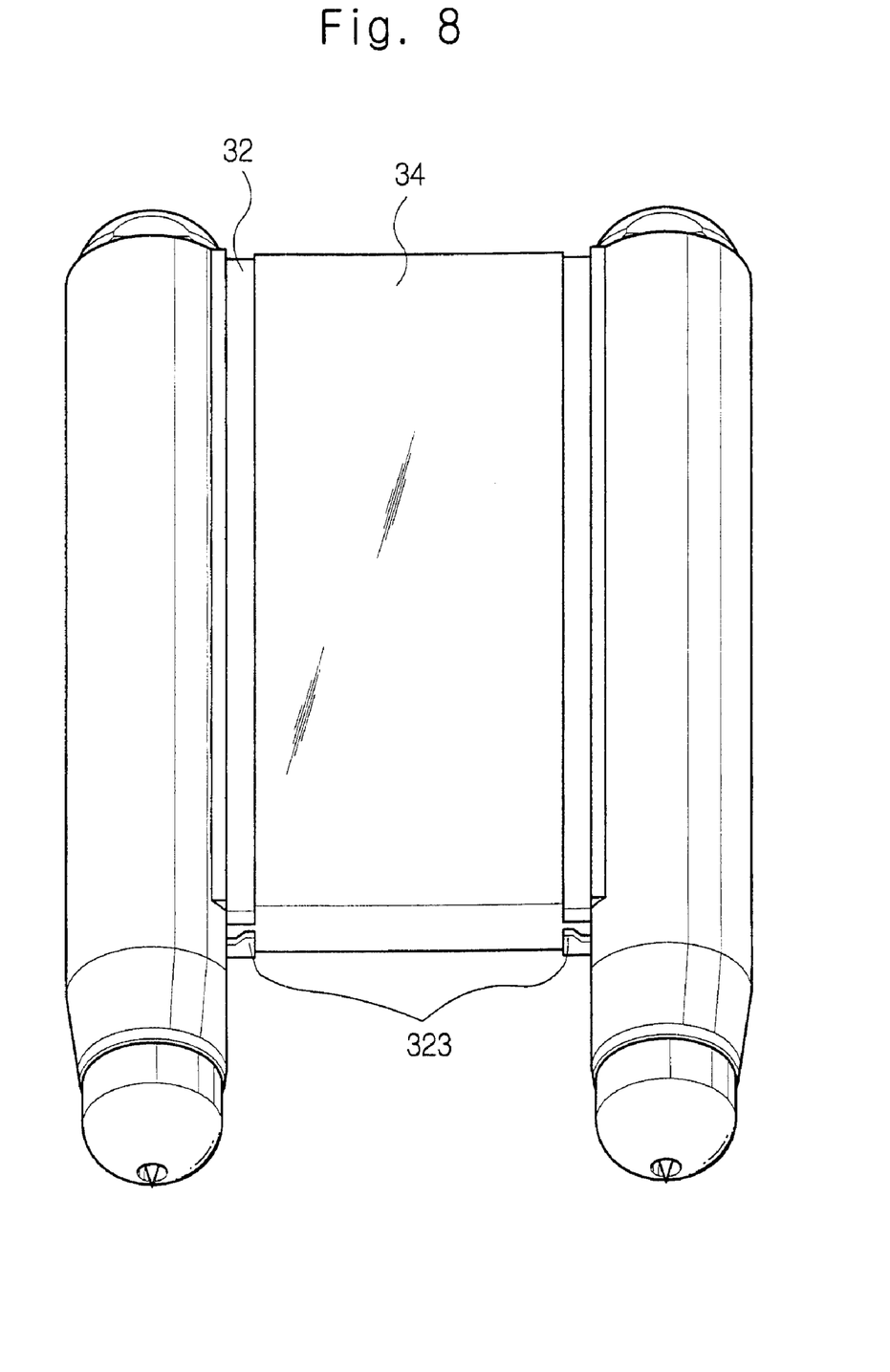
FIG. 8 is a perspective view, showing two treatment devices of this invention coupled together into a single system using a connection plate as desired.

FIG. 6 shows one device of this invention independently used. FIG. 8 shows two devices of this invention used at the same time while being coupled together into a single system.

When two or more devices of this invention are used at the same time while being coupled together into a single system as shown in FIG. 8, it is possible to effectively apply desired infrared rays, anions and lines of magnetic force from the devices onto a large area of the human body at the same time. The target spots, which require to be treated by the device of this invention, typically neighbor with each other on the human body, and so simultaneous use of the two or more devices on the neighboring target spots improves the medical treatment effect of the device.

In the preferred embodiment of the drawings, each device has one axial fitting channel 32 on the external surface of the casing 30. However, it should be understood that two or more axial fitting channels 32 may be formed on the external surface of the device without affecting the functioning of this invention. In such a case, it is possible to couple a plurality of devices together into a single system, in which the devices are arranged in a lattice arrangement. The devices, arranged in such a lattice arrangement, desirably effectively treat a larger area on the human body by applying far infrared rays, anions and lines of magnetic force onto the target spots within the area.

As described above, the external thread 35 is formed on the external surface of the lower end portion of the casing 30. A first annular magnet 31 is inserted into the lower end of the casing 30 so as to beset within the lower end portion of the casing 30. The first annular magnet 31, set within the casing 30, emits the lines of magnetic force, which are added to the lines of magnetic force generated from the magnet 13 seated in the magnet seat hole 151 of the support member 15, thus enhancing the lines of magnetic force. When such enhanced line the medical treatment for the human body caused by a magnetic field effect is more improved.

As best seen in FIG. 2, the interior surface of the lower end portion of the casing 30 is tapered so as to correspond to the tapered shape of the lower taper part 156 of the support member 15. A step is formed at the top end of the tapered interior surface of the casing 30 and stops the lower end of the annular step part 154 of the support member 15. Therefore, when the assembly, composed of the support member 15 fitted into the lower end of the coupling member 10, is inserted into the casing 30 downwardly from the top end of the casing 30, the insertion of the assembly is accomplished at a time the annular step part 154 of the support member 15 comes into contact with the step formed at the top end of the tapered interior surface of the casing 30.

An internally threaded cap 20, having a dome shape, is movably tightened to the external thread 35 of the casing 30. A part of or all of the above cap 20 is preferably made of a plastic material including a material capable of emitting far infrared rays or anions. The far infrared rays or anions are added to those radiated from the support member 15, and so the far infrared rays or anions radiated from the device are enhanced. For example, the lower part of the cap 20, seating a second annular magnet 21 therein, may be made of a material capable of emitting anions, while the upper part of the cap 20, having the internal thread engaging with the external thread 35 of the casing 30, may be made of a material capable of emitting far infrared rays. In the present invention, the cap 20 may be formed using such different materials while separately using the materials at divided parts as described above. Alternatively, the cap 20 may be formed using a mixture of the materials without dividing the cap 20 into parts. Such an alteration of use of the materials for the cap does not affect the functioning of this invention.

In the present invention, the far infrared rays or the anions are radiated from the cap 20 that is positioned close to the skin of the human body. Therefore, even though the quantity of the far infrared rays or the anions, radiated from the cap 20, is not sufficient, it is possible for the far infrared rays or anions to be effectively directly applied to the human body while being almost free from loss caused by leakage into the atmosphere, thus desirably activating the skin cells of the human body.

An internal thread is formed at the upper part of the internal surface of the cap 20 and engages with the external thread 35 of the casing 30 when the cap 20 is assembled with the casing 30. A needle hole 22 is formed at the center of the dome of the cap 20 and allows the needle tip 174 to pass through. The second annular magnet 21 is set in the central portion of the dome of the cap 20 and emits the lines of magnetic force. The lines of magnetic force, radiated from the second annular magnet 21, are added to the lines of magnetic force radiated from the magnet 13 of the support member 15 through the needle 17. In the preferred embodiment of the present invention, two annular magnets, or the first and second annular magnets 31 and 21, are separately set within the lower end of the casing 30 and the cap 20. However, it should be understood that either of the two annular magnets 21 and 31 may be removed from the device without affecting the functioning of this invention.

Figure 5:
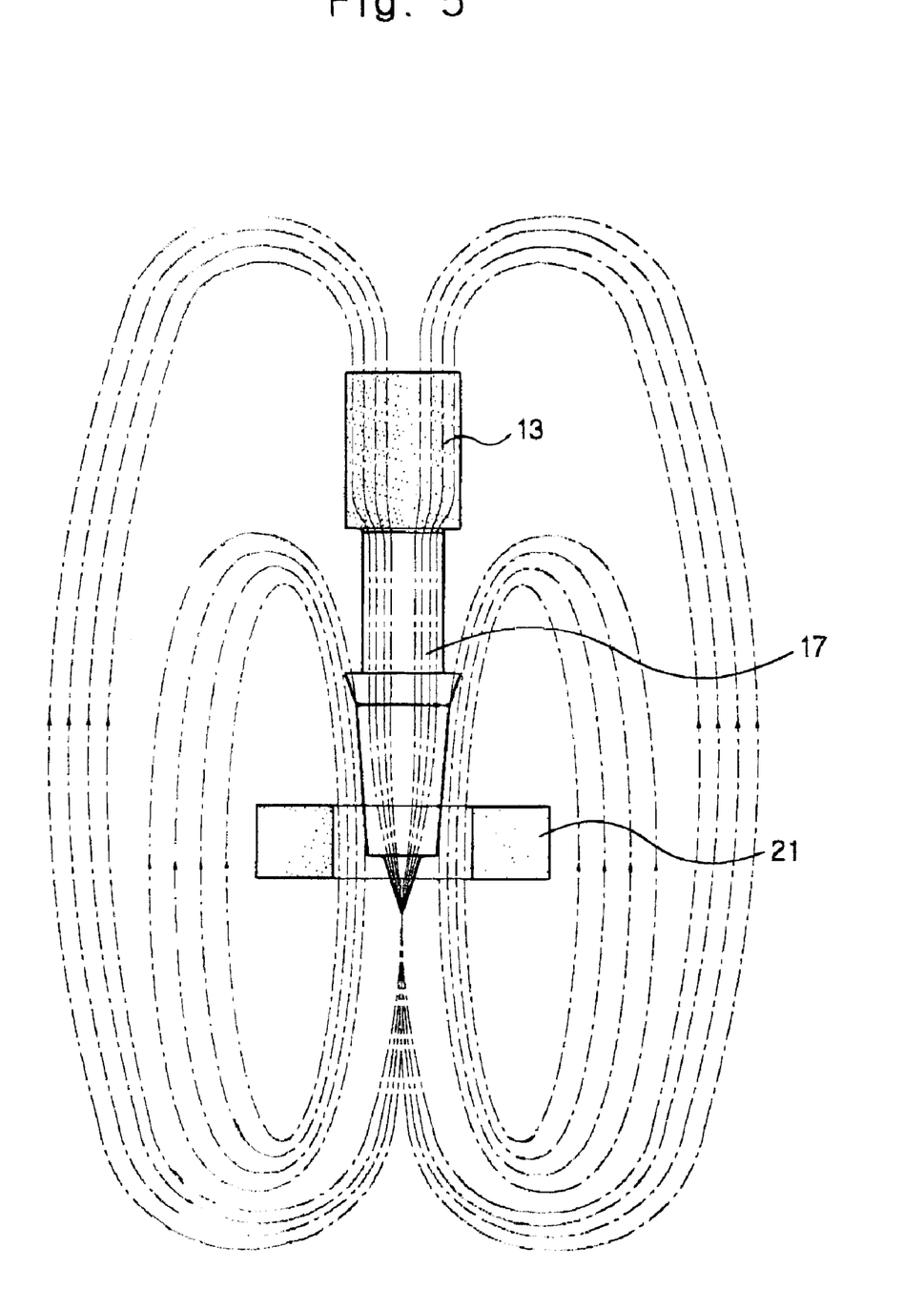
FIG. 5 is a view, showing the lines of magnetic force radiated from the treatment device of this invention.

FIG. 5 is a view, showing the lines of magnetic force radiated from the treatment device of this invention. The magnet 13 of the support member 15 radiates the lines of magnetic force as shown by the one-dot chain line in FIG. 5. On the other hand, the first and second annular magnets 31 and 21, separately set within the lower end of the casing 30 and the cap 20, radiate the lines of magnetic force as shown by the two-dot chain line of FIG. 5. The three magnets 13, 21 and 31 are appropriately positioned within the device of this invention in a way such that the magnetic fields formed by the three magnets are effectively mixed together and enhanced. Therefore, the intensity of magnetic field formed by the device of this invention is preferably increased. Such a high intensity of magnetic field is directly applied to a desired area of the skin of the human body, and so it is possible for the magnetic force of the magnets to be desirably deeply infiltrated into the human body.

In the device of this invention, it is possible for a user to freely adjust the exposed length of the needle tip 174 outside the needle hole 22 of the cap 20 as desired by appropriately moving the cap 20 relative to the casing 30.

Figure 7A:
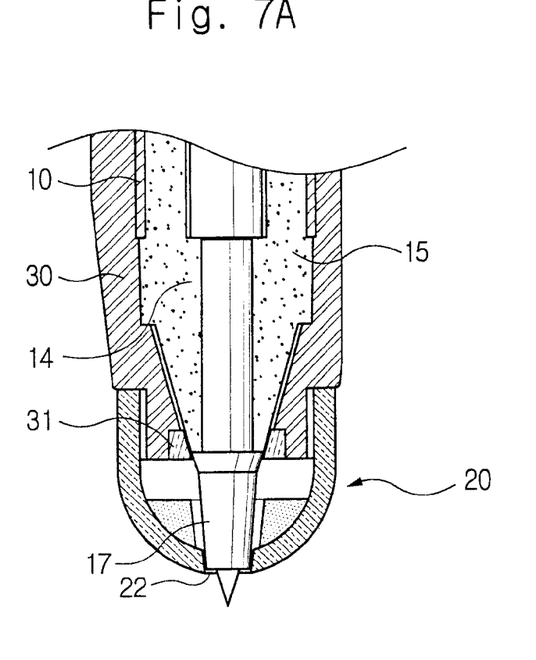
FIG. 7a is a sectional view, showing the cap fully retracted relative to the casing so as to allow an acupuncture needle of the device of this invention to be positioned at its fully protruded position.
Figure 7B:
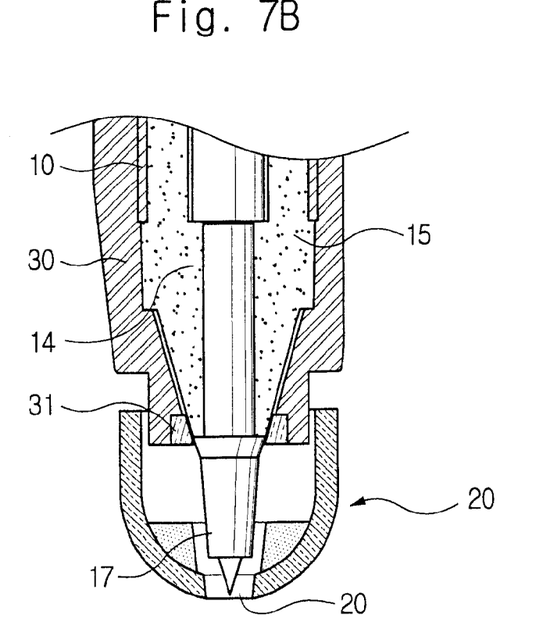
FIG. 7b is a sectional view, showing the cap fully extended relative to the casing so as to allow the acupuncture needle to be positioned at fully retracted position.

That is, when the cap 20 is fully tightened to the external thread 35 of the casing 30 as shown in FIG. 7a, the needle tip 174 of the device is positioned at its fully protruded position outside the needle hole 22 of the cap 20. On the other hand, when the cap 20 is loosened relative to the casing 30 as shown in FIG. 7b, the needle tip 174 of the device is positioned at its fully retracted position within the cap 20. In the fully retracted position of the needle 17, the tip 174 is not exposed outside the cap 20, but is completely covered by the cap 20.

In a medical treatment process using a conventional device for magnetic focus radiation treatment, healthy persons capable of easily enduring a strong stimulation or pain caused by a needle tip do not have a problem, and so it is possible for such healthy persons to accomplish a desired magnetic focus radiation medical treatment effect offered by such a conventional device. However, in the case of weak people, such as children or old people, it is very difficult to endure such a strong stimulation or pain caused by the needle tip, and so they do not want to take the magnetic focus radiation medical treatment, but are likely to avoid such a medical treatment. However, the device of this invention is designed to fully retract the needle tip 174 into the cap 20 when necessary as shown in FIG. 7b. It is thus possible for the device of this invention to effectively radiate desired far infrared rays, anions or lines of magnetic force onto the skin of the body of such weak people without giving any strong stimulation or pain to the people. This device thus desirably accomplishes a desired magnetic focus radiation medical treatment effect for weak people in addition to healthy people.

Figure 9:
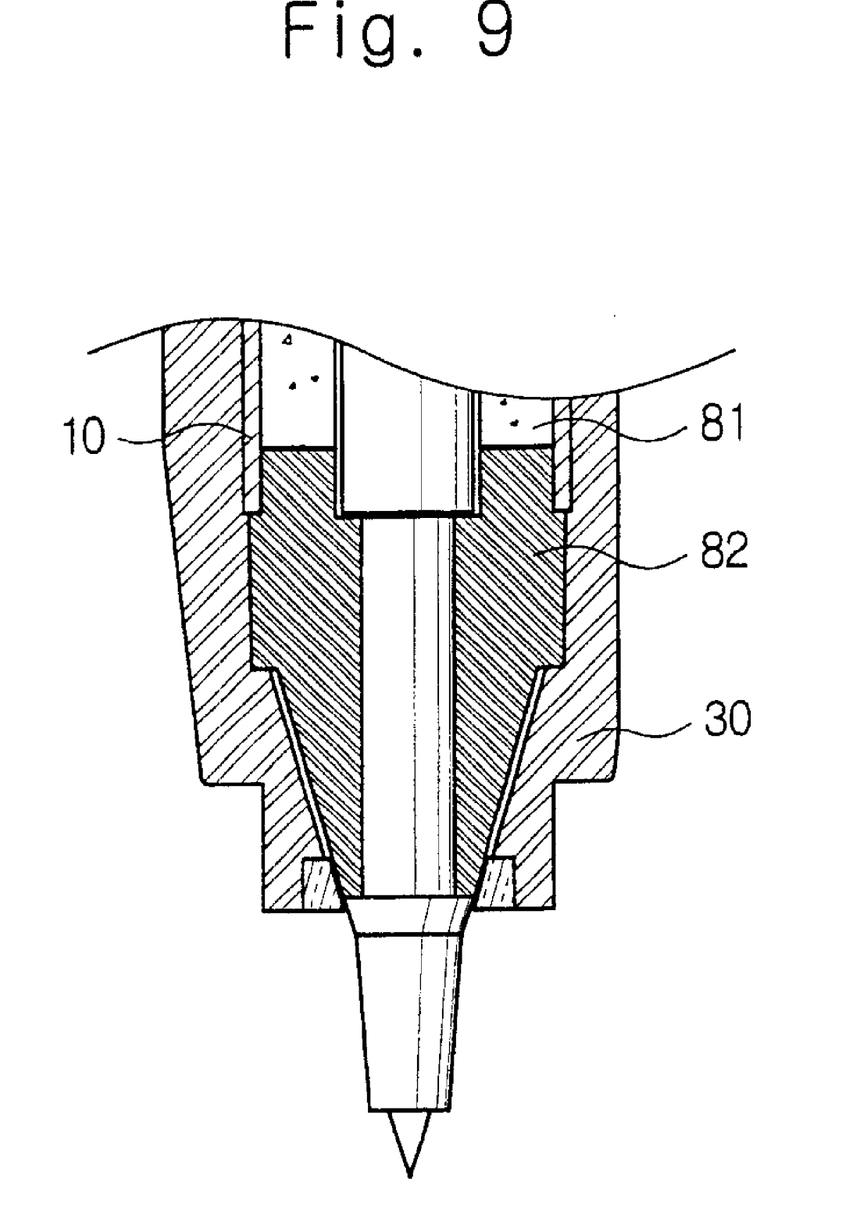
FIG. 9 is a sectional view, showing the construction of a support member of the treatment device in accordance with a modification of the preferred embodiment of this invention.

When a user carries the device of this invention, the cap safely covers the needle, thus protecting the user from the sharpened tip of the needle and protecting the needle from external impact. FIG. 9 is a sectional view, showing the construction of a support member of the medical treatment device in accordance with a modification of the preferred embodiment of this invention. In the modification of FIG. 9, the support member 15 is sectioned into two support parts, or a first support part 81 and a second support part 82, different from the support member 15 of FIGS. 1 and 2. The first support part 81 is used for holding the magnet 13 of the coupling member 13, while the second support part 82 is used for holding the needle 17. When the support part 15 is sectioned into the two parts 81 and 82 as described above, it is possible to separately make the two parts 81 and 82 using different appropriate materials meeting the specifically desired medical treatment effects expected by the two parts 81 and 82.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A device for magnetic focus radiating medical treatment, comprising:
   a support member holding both a magnet and a needle therein in a way such that the magnet comes into contact with the needle, said magnet being used for generating lines of magnetic force and said needle being used for radiating the lines of magnetic force from said magnet onto a desired part of the human body while concentrating the lines of magnetic force onto the desired part of the body;
   a hollow casing having a predetermined length and receiving said support member therein with a tip of said needle being selectively projected from a lower end of said casing, said casing having an external thread at said lower end thereof;
   an outside plug detachably covering a top end of said casing; and
   a cap movably tightened to the external thread of said casing, said cap having an internal thread at its upper portion and movably engaging with said external thread of the casing at the internal thread, said cap also having a needle hole at a central portion of its wall so as to allow the needle to pass through the needle hole,
   whereby an exposed length of said needle outside the cap is adjustable as desired by appropriately tightening or loosening the internally threaded cap relative to the externally threaded casing, wherein said support member is an integrated body composed of upper, middle and lower parts, with a magnet holding part provided at the upper part and a needle holding part provided at the lower part while communicating with the magnet holding part, said upper and lower parts of the support member being tapered, with an annular step part being formed on the middle part at a position around a junction between the middle and lower parts, said support part also having a plurality of axial grooves extending on an external surface of the support part at positions covering the middle part and the annular step part, said axial grooves of the middle part communicating with the axial grooves of the annular step part while being leveled with each other at their bottom surfaces.

2. The device according to claim 1, wherein said support member is fitted into a coupling member at its upper and middle parts prior to being set within the casing, with both the annular step part of the support member being seated on the end of the coupling member and an inside cap detachably covering the top end of the coupling member.

3. The device according to claim 2, wherein said coupling member is made of aluminum.

4. The device according to claim 1, wherein said support member and said cap are made of at least one material selected from the group consisting of an anion emitting material, a far infrared ray emitting material and a mixture thereof.

5. The device according to claim 4, wherein a reflection tap, made of aluminum, is detachably fitted into a top end of said support member, with a gap being formed between the lower part of said support member and an internal surface of said casing at a position corresponding to the lower part of the support member, and so anions or far infrared rays emitted from the support member are reflected by said reflection tap and are radiated through both the axial grooves of the middle and annular step parts of the support member and the gap formed between the lower part of the support member and the internal surface of the casing.

6. The device according to claim 1, wherein a first annular magnet is set within the hollow casing at a position around the second end of said casing.

7. The device according to claim 1, wherein a second annular magnet is set within the cap at a position around the needle hole of said cap.

8. The device according to claim 1, wherein said support member is sectioned into a magnet support part and a needle support part, said magnet and needle support parts part being continued and integrated into a single body at a junction between them.

9. A device for magnetic focus radiating medical treatment, comprising:
   a support member holding both a magnet and a needle therein in a way such that the magnet comes into contact with the needle, said magnet being used for generating lines of magnetic force and said needle being used for radiating the lines of magnetic force from said magnet onto a desired part of the human body while concentrating the lines of magnetic force onto the desired part of the body;
   a hollow casing having a predetermined length and receiving said support member therein with a tip of said needle being selectively projected from a lower end of said casing, said casing having an external thread at said lower end thereof;
   an outside plug detachably covering a top end of said casing; and
   a cap movably tightened to the external thread of said casing, said cap having an internal thread at its upper portion and movably engaging with said external thread of the casing at the internal thread, said cap also having a needle hole at a central portion of its wall so as to allow the needle to pass through the needle hole,
   whereby an exposed length of said needle outside the cap is adjustable as desired by appropriately tightening or loosening the internally threaded cap relative to the externally threaded casing, wherein at least one axial fitting channel is formed on the external surface of said casing by two parallel guide rails, one of the two parallel guide rails being projected inwardly along its top edge and a stop being formed at one end of said fitting channel.

10. The device according to claim 9, wherein said axial fitting channel of the casing axially selectively receives a first side edge of a connection plate therein, with a second side edge of the connection plate being fitted into the axial fitting channel of another casing, thus coupling two or more devices into a single system.

11. An acupuncture device, comprising:
   a casing having a generally cylindrical shape having a first end and a second end and being hollow with an axial bore having a hexagonal cross-section extending inward from the first end of the casing;
   an outside plug insertable into said first end of the casing;
   an external thread formed on the second end of the casing;
   a cap having an internal thread for engaging the external thread of the casing and adjustably positioning the cap, said cap having a central hole for allowing protrusion of the tip of an acupuncture needle; and an acupuncture needle assembly removably inserted into said hexagonal cross-sectioned axial bore of said casing, said acupuncture needle assembly comprising:
  a coupling member having a hollow hexagonal prismatic shape inserted into the axial bore of said casing toward said first end of the casing;
  a support member located near the second end of the casing, said support member being an integral part having a generally hexagonal cross-section with an upper end inserted into said coupling member, and having a needle seat hole formed in a lower end and a bore formed in the upper end of the support member, said support member further having axial grooves formed on the outer surface of the support member;
an acupuncture needle inserted into the needle seat hole;
a magnet having a cylindrical shape inserted into the bore of the support member;
a reflection tap inserted into the bore at the upper end of the support member; and
an internal cap inserted into the end of the coupling member nearer the first end of the casing.

12. The device of claim 11, further comprising:
the lower end of said support member having a conical taper; and
the axial bore of said casing having a conical taper toward the second end of the casing for accommodating the lower end of the support member.

13. The device of claim 11, further comprising:
the second end of said casing having an external diameter which is smaller than that of the rest of the casing.

14. The device of claim 11, further comprising:
said cap having a dome shape.

15. The device of claim 11, further comprising:
a cylindrical magnet mounted at the second end of the casing surrounding the lower end of said support member.

16. The device of claim 11, further comprising:
a cylindrical magnet mounted in said cap surrounding the acupuncture tip.

17. The device of claim 16, further comprising:
a cylindrical magnet mounted in said cap surrounding the acupuncture tip.

18. A method of using the acupuncture device of claim 11, comprising the steps of:
turning said cap to expose a desired portion of the acupuncture needle; and
holding said casing to press the acupuncture needle against a point on the skin of a person to be treated.

19. An acupuncture device, comprising:
a casing having a generally cylindrical shape having a first end and a second end and being hollow with an axial bore having a hexagonal cross-section extending inward from the first end of the casing;
an outside plug insertable into said first end of the casing;
an external thread formed on the second end of the casing;
a cap having an internal thread for engaging the external thread of the casing and adjustably positioning the cap, said cap having a central hole for allowing protrusion of the tip of an acupuncture needle; and
an acupuncture needle assembly removably inserted into said hexagonal cross-sectioned axial bore of said casing, said acupuncture needle assembly comprising:
  a coupling member having a hollow hexagonal prismatic shape inserted into the axial bore of said casing toward said first end of the casing;
  a support member located near the second end of the casing, said support member being an integral part having a generally hexagonal cross-section with an upper end inserted into said coupling member, and having a needle seat hole formed in a lower end and a bore formed in the upper end of the support member, said support member further having an annular step part formed on the exterior of the support member, for positioning the support member in the coupling member;
an acupuncture needle inserted into the needle seat hole;
a magnet having a cylindrical shape inserted into the bore of the support member;
a reflection tap inserted into the bore at the upper end of the support member; and
an internal cap inserted into the end of the coupling member nearer the first end of the casing.

20. An acupuncture device, comprising:
a casing having a generally cylindrical shape having a first end and a second end and being hollow with an axial bore having a hexagonal cross-section extending inward from the first end of the casing;
an outside plug insertable into said first end of the casing;
an external thread formed on the second end of the casing;
a cap having an internal thread for engaging the external thread of the casing and adjustably positioning the cap, said cap having a central hole for allowing protrusion of the tip of an acupuncture needle; and
an acupuncture needle assembly removably inserted into said hexagonal cross-sectioned axial bore of said casing, said acupuncture needle assembly comprising:
  a coupling member having a hollow hexagonal prismatic shape inserted into the axial bore of said casing toward said first end of the casing;
  a support member located near the second end of the casing, said support member being an integral part having a generally hexagonal cross-section with an upper end inserted into said coupling member, and having a needle seat hole formed in a lower end and a bore formed in the upper end of the support member;
  an acupuncture needle inserted into the needle seat hole;
  a magnet having a cylindrical shape inserted into the bore of the support member;
  a reflection tap inserted into the bore at the upper end of the support member; and
  an internal cap inserted into the end of the coupling member nearer the first end of the casing, said acupuncture device further comprising:
a fitting channel formed lengthwise along the exterior of the casing; and
a stop formed at the bottom of the fitting channel; and
a connection plate having two edges on opposite sides of the plate, one edge inserted into the fitting channel of said casing and the second edge inserted into the fitting channel of the casing of a second of said acupuncture devices.

21. The device of claim 20, further comprising:
a second fitting channel formed lengthwise along the exterior of the casing opposite said first fitting channel, for receiving a edge of a second connection plate.

22. A method of using the acupuncture device of claim 21, comprising the steps of:

turning the caps of the two acupuncture devices to expose the desired portions of the acupuncture needles; and holding the two acupuncture devices against two respective points on the skin of a person to be treated.

* * * * *